(12) United States Patent
Schiff et al.

(10) Patent No.: US 11,419,976 B1
(45) Date of Patent: Aug. 23, 2022

(54) WEARABLE DRUG DELIVERY DEVICE WITH PRESSURIZED FLUID DISPENSING

(71) Applicant: Fresenius Kabi Deutschland GmbH, Bad Homburg (DE)

(72) Inventors: David R. Schiff, Highland Park, NJ (US); Sharon D. West, Elkins Park, PA (US)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 17/246,198

(22) Filed: Apr. 30, 2021

(51) Int. Cl.
*A61M 5/142* (2006.01)
*A61M 5/168* (2006.01)
*A61M 5/145* (2006.01)

(52) U.S. Cl.
CPC ...... *A61M 5/14248* (2013.01); *A61M 5/1452* (2013.01); *A61M 5/16881* (2013.01); *A61M 2005/14252* (2013.01); *A61M 2202/0007* (2013.01)

(58) Field of Classification Search
CPC ............ A61M 5/14248; A61M 5/1452; A61M 5/16881; A61M 5/148; A61M 5/1483; A61M 5/152; A61M 5/155
See application file for complete search history.

(56) References Cited

U.S. PATENT DOCUMENTS

| 5,290,240 | A | * | 3/1994 | Homes, Jr. ............ | A61M 5/145 604/141 |
| 6,620,134 | B1 | * | 9/2003 | Trombley, III ... | A61M 5/14546 604/133 |
| 2003/0167036 | A1 | | 9/2003 | Flaherty | |
| 2004/0116866 | A1 | | 6/2004 | Gorman et al. | |
| 2004/0199123 | A1 | | 10/2004 | Nielsen | |
| 2008/0091139 | A1 | | 4/2008 | Srinivasan et al. | |
| 2008/0125700 | A1 | | 5/2008 | Moberg et al. | |
| 2009/0131860 | A1 | | 5/2009 | Nielsen | |
| 2010/0137832 | A1 | | 6/2010 | Mathews et al. | |
| 2010/0262078 | A1 | | 10/2010 | Blomquist | |
| 2011/0178461 | A1 | | 7/2011 | Chong et al. | |

(Continued)

FOREIGN PATENT DOCUMENTS

| WO | 2018081234 A1 | 5/2018 |
| WO | 2018183039 A1 | 10/2018 |

(Continued)

*Primary Examiner* — Nathan R Price
*Assistant Examiner* — Tasnim Mehjabin Ahmed
(74) *Attorney, Agent, or Firm* — Cook Alex Ltd.

(57) ABSTRACT

A drug delivery device has a housing with an adhesive pad associated with the lower surface of the housing and configured to removably attach to a human body surface. A drug reservoir is positioned within the housing and includes an outlet with a valve, with a needle fluidically connected to the reservoir and configured to define at least a portion of a fluid flow path between the reservoir and the human body surface. A controller is configured to control the components of the drug delivery device to execute a drug delivery routine. The drug delivery device also includes pressurized fluid positioned to apply a force to the reservoir. The controller moves the valve from a closed condition to an open condition during a drug delivery routine to allow the pressurized fluid to deform the reservoir or move a plunger to convey the drug out of the reservoir via the outlet.

20 Claims, 4 Drawing Sheets

(56) References Cited

U.S. PATENT DOCUMENTS

| | | | |
|---|---|---|---|
| 2011/0196304 A1* | 8/2011 | Kramer | A61M 5/1483 604/151 |
| 2012/0010594 A1 | 1/2012 | Holt et al. | |
| 2015/0374919 A1 | 12/2015 | Gibson | |
| 2016/0038689 A1 | 2/2016 | Lee et al. | |
| 2016/0082182 A1 | 3/2016 | Gregory et al. | |
| 2016/0175515 A1* | 6/2016 | McCullough | A61M 5/14248 604/65 |
| 2016/0199574 A1 | 7/2016 | Ring et al. | |
| 2016/0220798 A1 | 8/2016 | Netzel et al. | |
| 2016/0296704 A1 | 10/2016 | Gibson | |
| 2016/0354555 A1 | 12/2016 | Gibson et al. | |
| 2017/0119969 A1 | 5/2017 | McCullough et al. | |
| 2017/0124284 A1 | 5/2017 | McCullough et al. | |
| 2017/0147787 A1 | 5/2017 | Albrecht et al. | |
| 2017/0182253 A1 | 6/2017 | Folk et al. | |
| 2017/0340837 A1 | 11/2017 | Nazzaro et al. | |
| 2017/0361015 A1 | 12/2017 | McCullough | |
| 2017/0368260 A1 | 12/2017 | McCullough et al. | |
| 2018/0021508 A1 | 1/2018 | Destefano et al. | |
| 2018/0028747 A1 | 2/2018 | Hanson et al. | |
| 2018/0036476 A1 | 2/2018 | McCullough et al. | |
| 2018/0085517 A1 | 3/2018 | Laurence et al. | |
| 2018/0256823 A1 | 9/2018 | Nazzaro et al. | |
| 2018/0272059 A1 | 9/2018 | Marbet et al. | |
| 2018/0304014 A1 | 10/2018 | Knudsen et al. | |
| 2019/0009019 A1* | 1/2019 | Shor | A61M 5/1782 |
| 2019/0022306 A1 | 1/2019 | Gibson et al. | |
| 2019/0050375 A1 | 2/2019 | Fitzgibbon et al. | |
| 2019/0060562 A1 | 2/2019 | Olivas et al. | |
| 2019/0083702 A1 | 3/2019 | Nekouzadeh et al. | |
| 2019/0134296 A1 | 5/2019 | Barbedette et al. | |
| 2019/0143043 A1 | 5/2019 | Coles et al. | |
| 2019/0143047 A1 | 5/2019 | Jazayeri et al. | |
| 2019/0151544 A1 | 5/2019 | Stonecipher | |
| 2019/0167908 A1 | 6/2019 | Fitzgibbon et al. | |
| 2019/0192766 A1 | 6/2019 | Stonecipher | |
| 2019/0247579 A1 | 8/2019 | Damestani et al. | |
| 2019/0275241 A1 | 9/2019 | Ring et al. | |
| 2019/0328965 A1 | 10/2019 | Moberg | |
| 2019/0365986 A1 | 12/2019 | Coiner et al. | |
| 2019/0374707 A1 | 12/2019 | Damestani et al. | |
| 2019/0381238 A1 | 12/2019 | Stonecipher et al. | |
| 2020/0023122 A1 | 1/2020 | McCullough et al. | |
| 2020/0164145 A1 | 5/2020 | Chang et al. | |
| 2020/0164155 A1 | 5/2020 | Mojarrad et al. | |
| 2020/0179609 A1 | 6/2020 | Tan-Malecki et al. | |
| 2020/0197628 A1 | 6/2020 | McCullough et al. | |
| 2020/0206429 A1 | 7/2020 | Hering et al. | |
| 2020/0230313 A1 | 7/2020 | Mojarrad et al. | |
| 2020/0238004 A1 | 7/2020 | McCullough | |
| 2020/0254172 A1 | 8/2020 | Forster et al. | |
| 2020/0261643 A1 | 8/2020 | Boyaval et al. | |
| 2020/0261648 A1 | 8/2020 | Groszmann et al. | |
| 2020/0261657 A1 | 8/2020 | Gibson et al. | |
| 2020/0289745 A1 | 9/2020 | Harris et al. | |
| 2020/0297927 A1 | 9/2020 | Conrath et al. | |
| 2020/0322793 A1 | 10/2020 | Yang | |
| 2020/0338271 A1 | 10/2020 | Harris et al. | |

FOREIGN PATENT DOCUMENTS

| | | |
|---|---|---|
| WO | 2018226565 A1 | 12/2018 |
| WO | 2019018169 A1 | 1/2019 |
| WO | 2019022950 A1 | 1/2019 |
| WO | 2019022951 A1 | 1/2019 |
| WO | 2019032101 A1 | 2/2019 |
| WO | 2019143753 A1 | 7/2019 |

* cited by examiner

WEARABLE DRUG DELIVERY DEVICE WITH PRESSURIZED FLUID DISPENSING

BACKGROUND

Field of the Disclosure

The present disclosure relates to drug delivery devices. More particularly, the present disclosure relates to devices mounted to the body utilizing pressurized fluid to deliver a drug to a patient.

Description of Related Art

Delivery of liquid drugs to a patient via injection using a needle or syringe is well-known. More recently, devices that automate the delivery of liquid drugs have been introduced. These devices (which are commonly referred to as "on-body devices" or "on-body injectors") are mounted or otherwise secured to the body of the patient (e.g., to the arm or abdomen) and remain in place for an extended amount of time (on the order of hours or days), injecting an amount of the drug into the body of the patient at one or more scheduled times. For example, a device may be configured to deliver a drug over the span of 45 minutes, with delivery beginning 27 hours after the device has been activated and applied to a patient (to ensure that the drug is not delivered sooner than 24 hours after a medical procedure or treatment). These devices improve upon manual methods by obviating the need for the patient to inject themselves with the drug (which carries heightened risks of the patient improperly administering the injection or injecting the drug at an inappropriate time) or to return to a medical facility for one or more injections by a technician or medical professional.

One known on-body device 10 is shown in FIGS. 1 and 2. The device 10 of FIG. 1 includes a housing 12 that contains or encloses the functional components of the device 10, which are shown in FIGS. 3 and 4.

The internal components of the device 10 include a reservoir 14 that is configured to be filled with a liquid drug to be delivered to the patient. An upper surface of the housing 12 includes a fill indicator 16 that provides a visual indication of the amount of fluid in the reservoir 14. In addition to the fill indicator 16, the upper surface of the housing 12 may include printed information, such as information regarding the drug to be delivered. The upper surface of the housing 12 may be formed of a translucent material, which allows light from a status light 18 (which may be configured as a light-emitting diode) mounted within the housing 12 (FIG. 1) to be seen through the upper surface of the housing 12. The status light 18 is electrically coupled to a controller or processor (which may be a CPU or MPU configured as a computer chip mounted to a printed circuit board positioned within the housing 12, for example) that carries software for executing a drug delivery routine. The status light 18 receives signals from the controller and emits light to provide information regarding a status of the device 10. This may include emitting differently colored light and/or emitting light in different flashing patterns to indicate different conditions, such as a blinking orange light to indicate that the device 10 is ready to be applied to a patient, a blinking green light to indicate proper operation of the device 10, and a blinking red light to indicate an error or other condition. One or more batteries 20 provides power to the status light 18 and the other electrical components of the device 10.

The drug is injected into the reservoir 14 using a (typically pre-filled) syringe 22 via a port 24 incorporated into the bottom or underside of the housing 12 (FIG. 4) and fluidically connected to the reservoir 14. FIGS. 1 and 2 illustrate an applicator 26 that is removably associated with the underside of the housing 12 and used in combination with the syringe 22 to fill the reservoir 14 via the port 24. The drug is most typically injected into the reservoir 14 by a medical professional immediately before the device 10 is secured to the patient to ensure that the proper drug is supplied, along with the proper amount.

A piston or plunger 28 (FIG. 4) positioned within the reservoir 14 is moved (from left to right, in the orientation of FIG. 4) as the space within the reservoir 14 is filled by the inflowing drug. Movement of the piston 28 into its final position (when the reservoir 14 has been filled with the appropriate amount of the drug) causes a portion of a rod associated with the piston 28 to extend from the reservoir 14 to create an electrical connection, which activates the device 10. Activation of the device 10 may include a signal, such as a buzzer providing an audible indication that the device 10 has been activated and/or a light emitted by the status light 18.

When the device 10 has been activated, it is mounted or secured to the body of the patient. The applicator 26 is first removed from the underside of the housing 12 and discarded, followed by a pull tab 30 being manipulated to remove a release film from an adhesive pad 32 associated with the underside of the housing 12. The housing 12 is then pressed against the body of the patient, with the adhesive pad 32 facing the body. An adhesive present on the adhesive pad 32 causes the adhesive pad 32 (and, hence, the housing 12) to adhere to the body.

Some predetermined time after the device 10 has been activated (which may be on the order of three to five minutes, for example), a distal end portion of a cannula 34 is introduced into the skin of the patient via a cannula window 36 defined in the housing 12 (FIGS. 3 and 4). The cannula 34 (which remains partially positioned within the skin of the patient for as long as the device 10 is in use) is formed of a flexible or semi-rigid material, such as a plastic material, for improved patient comfort.

As the cannula 34 is not itself configured to pierce the skin, an associated needle 38 is provided within the lumen of the cannula 34, with a sharp or beveled distal end of the needle 38 extending out of a distal end of the cannula 34. A midsection of the needle 38 is mounted within a needle carriage 40, while a proximal end 42 of the cannula 34 is mounted within a cannula carriage 44 that is initially positioned directly adjacent to the needle carriage 40. The needle carriage 40 is pivotally connected to an end of a linkage or crank arm 46, with an opposite end of the linkage 46 being associated with a torsion spring 48. At the designated time (e.g., 3-5 minutes after the device 10 has been activated), the controller causes a lever (not visible) to be released, which allows the spring 48 to recoil, in turn rotating the linkage 46, which rotation causes the needle carriage 40 to move along a linear track 50 from a first position adjacent to the spring 48 (FIG. 3) to a second position spaced away from the spring 48. Movement of the needle carriage 40 causes corresponding movement of the cannula carriage 44 along the track 50, with the cannula 34 and the distal portion of the needle 38 moving together in a direction away from the spring 48. Moving the carriages 40 and 44 into the second position causes the sharp distal end of the needle 38 to advance out of the housing 12 via the cannula window 36 and pierce the skin. The cannula 34 is carried by or moves along with the distal portion of the needle 38, such that the needle 38 piercing the skin will also cause the distal end of the cannula 34 to enter into the skin.

Continued recoiling of the spring 48 causes further rotation of the linkage 46, which has the effect of moving the needle carriage 40 back toward the spring 48 (i.e., back toward its first position). Rather than moving along with the needle carriage 40, the cannula carriage 44 is held in its second position (FIG. 3) by a lock or latch 52. As the movement of the needle carriage 40 is not restricted by the lock or latch 52, the needle carriage 40 will return to its first position, while the cannula carriage 44 remains in its second position (with the final positions of both carriages 40 and 44 shown in FIG. 3).

Movement of the needle carriage 40 in a proximal direction away from the cannula carriage 44 causes the needle 38 to partially (but not fully) retract from the cannula 34. In the final condition shown in FIG. 3, the distal end of the needle 38 is positioned within the cannula 34 (e.g., adjacent to a midsection or midpoint of the cannula 34), while the distal end of the cannula 34 remains positioned within the skin. A proximal end of the needle 38 extends into fluid communication with the reservoir 14, such that the needle 38 provides a fluid path from the reservoir 14 to the cannula 34 when the carriages 40 and 44 are in the final condition illustrated in FIG. 3. Due to the distal end of the cannula 34 remaining positioned within the skin, subsequent advancement of the drug out of the reservoir 14 (e.g., 27 hours after the device 10 has been activated) will cause the drug to move into the needle 38 (via the proximal end of the needle 38), through the needle 38 (to its distal end), and into the cannula 34. The drug is then delivered to the patient (e.g., over the course of a 45-minute session) via the distal end of the cannula 34 positioned within the skin.

As for the mechanism by which the drug is advanced out of the reservoir 14, the device 10 includes a lever 54 mounted to a pivot point 56 (FIG. 4). The lever 54 includes a first arm 58 configured and oriented to interact with a first gear 60 and a second arm 62 configured and oriented to interact with a second gear 64. A tab 66 extends from an opposite end of the lever 54 and is configured and oriented to alternately move into and out of contact with two electrical contacts 68 and 70 (electrically coupled to a printed circuit board, which is not shown) as the lever 54 pivots about the pivot point 56.

A first wire or filament 72 extends from the lever 54, around a first pulley 74, and into association with a first electrical contact 76. A second wire or filament 78 extends from the lever 54 in the opposite direction of the first wire 72, around a second pulley 80, and into association with a second electrical contact 82. The wires 72 and 78 (which are commonly referred to as "muscle wires") are formed of a shape memory alloy (e.g., Nitinol), which causes them to heat up and contract when a current flows through them, while being allowed to stretch when the current is removed and the wire 72, 78 cools. Current is alternately applied to the two wires 72 and 78, causing the one carrying a current to heat up and contract while the other one is allowed to stretch. The wire 72, 78 that contacts will pull on the lever 54, causing it to pivot about the pivot point 56. Thus, alternately applying current to the two wires 72 and 78 will cause the wires 72 and 78 to alternately contact and stretch, which in turn causes the lever 54 to pivot back and forth about the pivot point 56.

At the designated time (e.g., 27 hours after the device 10 has been activated), the controller provides commands that cause current to be alternately applied to the muscle wires 72 and 78, which causes the lever 54 to alternately pivot about the pivot point 56 in opposite first and second directions. Pivotal movement of the lever 54 in the first direction will cause the first arm 58 of the lever 54 to engage and rotate the first gear 60 an incremental amount, while pivotal movement of the lever 54 in the second direction will cause the second arm 62 of the lever 54 to engage and rotate the second gear 64 an incremental amount (in the same direction in which the first gear 60 is rotated by the first arm 58). Both gears 60 and 64 are associated with a common shaft 84 (which is shown in FIG. 3 and may be formed with the gears 60 and 64 as a single, molded piece), such that rotation of either gear 60, 64 will cause the shaft 84 to rotate about its central axis. The shaft 84 is mechanically coupled to the piston 28 within the reservoir 14, with rotation of the shaft 84 causing the piston 28 to move toward its initial position (e.g., by a threaded connection whereby rotation of the shaft 84 is translated into movement of the piston 28 along the length of the reservoir 14). As the piston 28 moves toward its initial position (from right to left in the orientation of FIG. 4), it will force the drug out of the reservoir 14 via the proximal end of the needle 38. As described above, the drug will flow through the needle 38, into and through the cannula 34, and into the body of the patient.

After the drug has been delivered (e.g., over the course of a 45-minute session), the controller alerts the patient via a visual cue from the status light 18 and/or an audible cue from the buzzer that drug delivery is complete. Subsequently, the patient removes the device 10 from their skin and discards the device 10.

While devices of the type described above have proven adequate, there is room for improvement of them. For example, the size and the profile of the device can be greatly improved. This can be done by reducing the size of the drug reservoir and/or reducing the on-board power requirement with alternate force mechanisms. A lower and more compact profile can provide a more comfortable device for the user and reduce instances of devices being caught on clothing, preventing accidental leakage from the device.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a drug delivery device comprises a housing, an adhesive pad associated with the lower surface of the housing and configured to removably attach to a human body surface, a deformable drug reservoir positioned within the housing and including an outlet with a valve, and a needle fluidically connected to the drug reservoir and configured to define at least a portion of a fluid flow path between the drug reservoir and said human body surface. The drug delivery device also includes a controller configured to control the components of the drug delivery device to execute a drug delivery routine and a pressurized fluid positioned between the housing and the drug reservoir. The controller is configured to control the valve to move from a closed condition to an open condition during said drug delivery routine so as to allow the pressurized fluid to deform the drug reservoir, thereby conveying a drug out of the drug reservoir via the outlet.

In another aspect, a drug delivery device comprises a housing, an adhesive pad associated with the lower surface of the housing and configured to removably attach to a human body surface, a drug reservoir positioned within the housing and including an outlet with a valve, a plunger positioned within the drug reservoir, separating an interior of the drug reservoir into first and second chambers, and a needle fluidically connected to the drug reservoir and configured to define at least a portion of a fluid flow path between the drug reservoir and said human body surface. The drug delivery device also includes a controller configured to control the components of the drug delivery device to execute a drug delivery routine and a pressurized fluid positioned within the first chamber of the drug reservoir. The controller is configured to control the valve to move from a closed condition to an open condition during said drug delivery routine so as to allow the pressurized fluid to move the plunger toward the outlet, thereby conveying a drug positioned within the second chamber out of the drug reservoir via the outlet.

This and other aspects of the present subject matter are set forth in the following detailed description of the accompanying drawings.

DESCRIPTION OF THE ILLUSTRATED EMBODIMENTS

Figure 1:
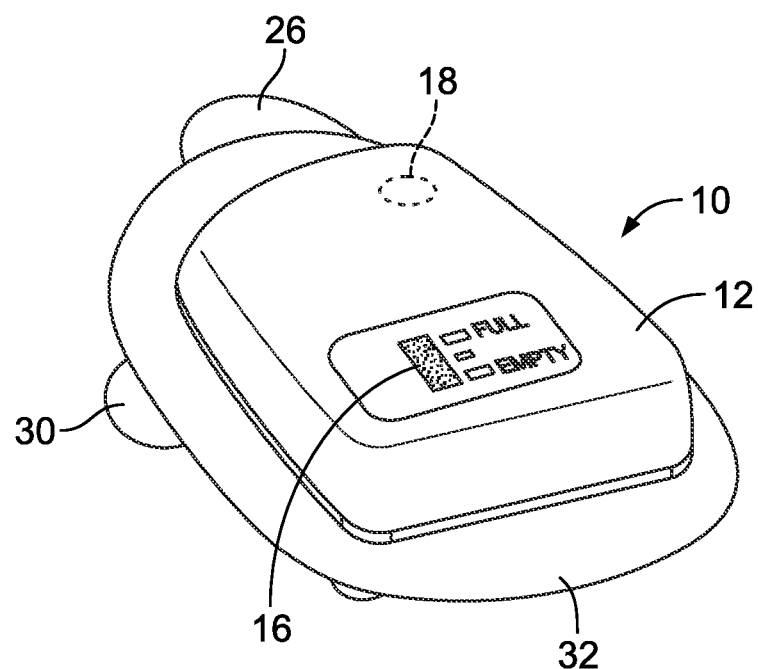
FIG. 1 is a top perspective view of a drug delivery device according to conventional design.
Figure 2:
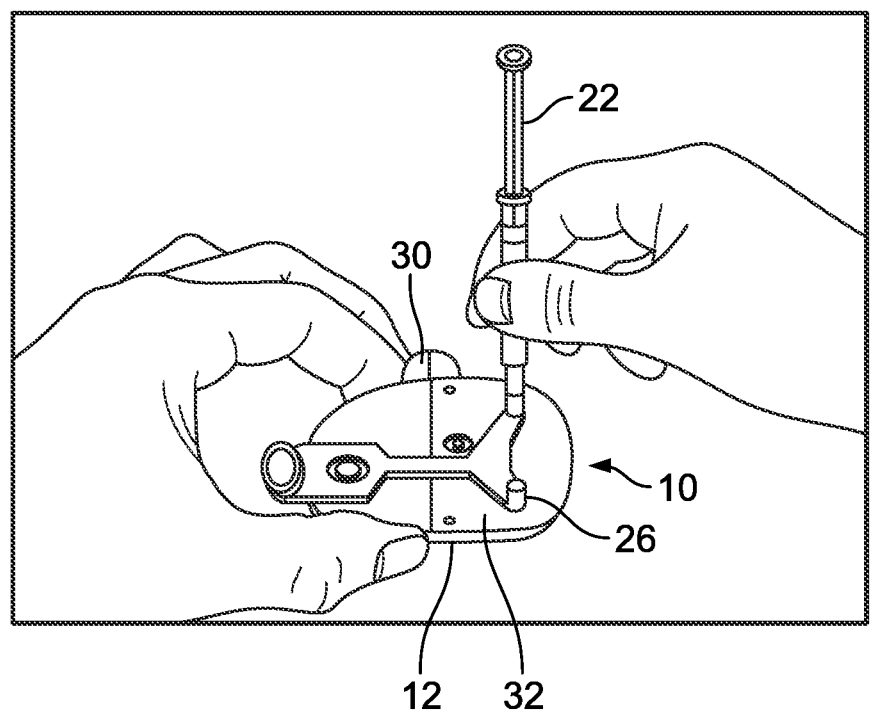
FIG. 2 is a bottom perspective view of the drug delivery device of FIG. 1.
Figure 3:
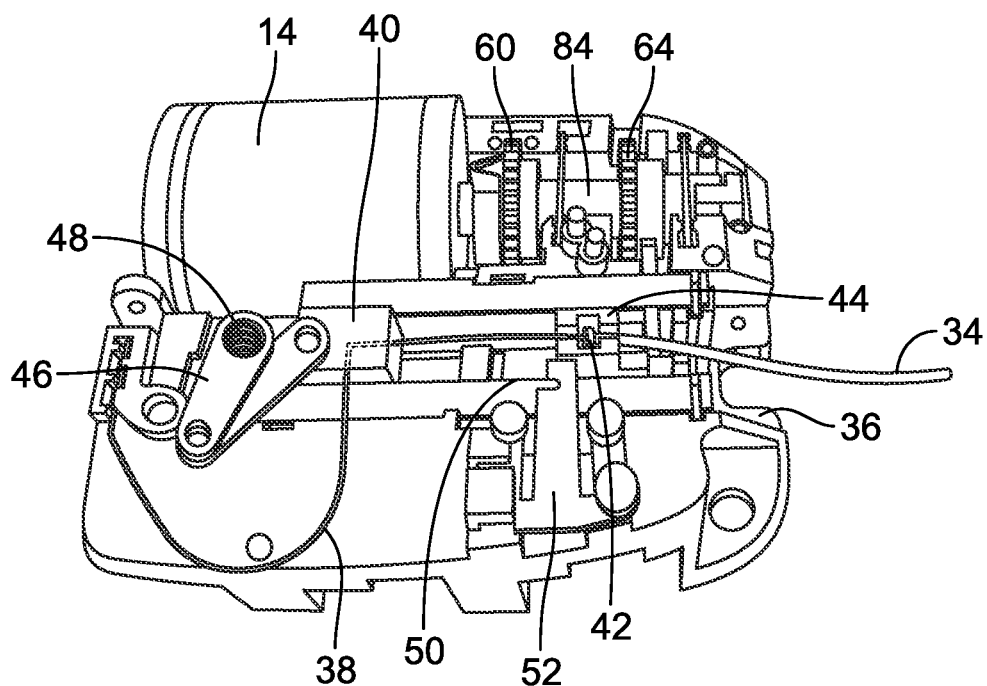
FIG. 3 is a top perspective view of the interior components of the drug delivery device of FIG. 1.
Figure 4:
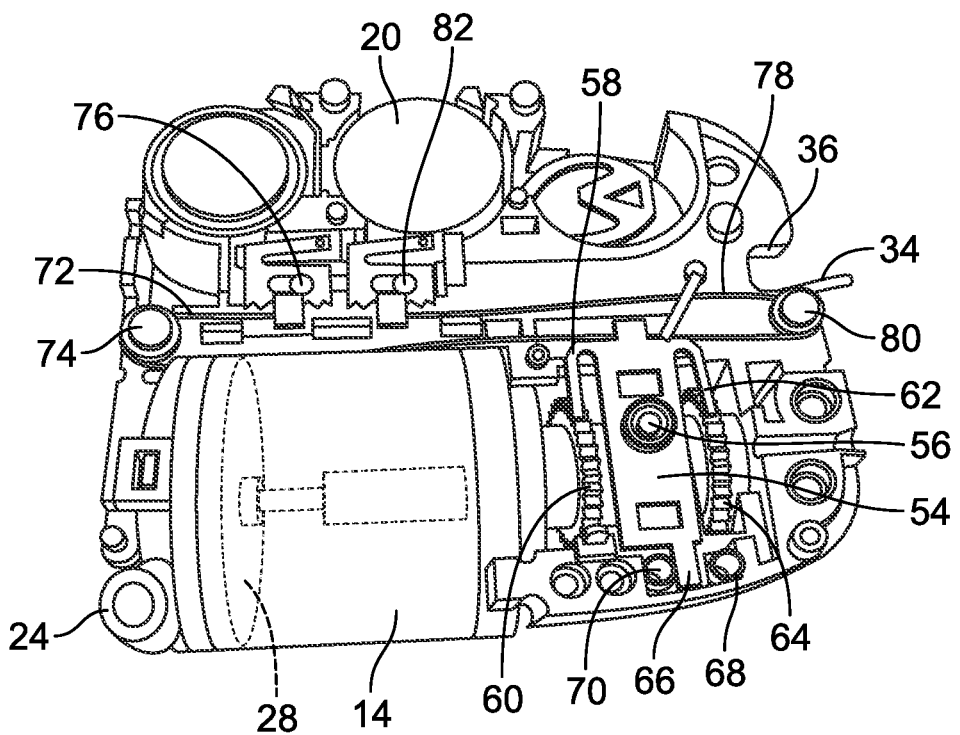
FIG. 4 is a bottom perspective view of the interior components of the drug delivery device of FIG. 1.

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

In contrast to the conventional device described above and shown in FIGS. 1-4, devices according to the present disclosure employ pressurized fluid to convey a drug out of a drug reservoir. One advantage of such an approach is its versatility, as differently configured drug reservoirs may be used in combination with a pressurized fluid, which may include a deformable drug reservoir (FIGS. 5 and 6) and a generally rigid drug reservoir (FIGS. 7 and 8), though it should be understood that the illustrated drug reservoir and pressurized fluid combinations are merely exemplary and that other combinations may be employed without departing from the scope of the present disclosure. Another advantage of the use of pressurized fluid is that it allows for a reduction in the number of (possibly bulky) mechanical parts required to be incorporated into a device, which in turn allows for the device to be smaller. This may include a reduction in the size of an onboard battery or power source, as less power may be needed to execute a drug delivery routine than is required by a conventional device with more mechanical components.

While the drug reservoir of FIGS. 5 and 6 differs from the drug reservoir of FIGS. 7 and 8 (as will be explained in greater detail), the respective drug delivery devices 110 and 210 may otherwise be similarly configured, with similar components being numbered similarly throughout the Figures. In both embodiments, the drug delivery device 110/210 includes a housing 116/216. The housing 116/216 contains or encloses the functional components of the device 110/210, including a controller 118/218 and the drug reservoir 112/212. The reservoir 112/212 is configured to be filled with a liquid drug to be delivered to a patient, with the reservoir 112/212 being filled either before or after the reservoir 112/212 is mounted within the housing 116/216, which may include the reservoir 112/212 being filled by a medical professional shortly before the device 110/210 is activated for a drug delivery routine.

The methods and devices described herein may be used to deliver any suitable fluid medication to a subject. In an exemplary embodiment, the methods and devices described herein are used to deliver pegfilgrastim to a subject, though other exemplary medications include (without limitation) one or more of the following: adalimumab, rituximab, risankizumab, etanercept, trastuzumab, ado-trastuzumab emtansine, trastuzumab deruxtecan, bevacizumab, infliximab, pegfilgrastim, filgrastim, tocilizumab, golimumab, interferon beta-1a, ranibizumab, denosumab, pembrolizumab, nivolumab, aflibercept, eculizumab, ocrelizumab, pertuzumab, secukinumab, omalizumab, ustekinumab, vedolizumab, daratumumab, dupilumab, atezolizumab, natalizumab, bortezomib, ipilimumab, durvalumab, emicizumab, palivizumab, guselkumab, mepolizumab, panitumumab, ramucirumab, belimumab, abatacept, certolizumab pegol, ixekizumab, romiplostim, benralizumab, evolocumab, canakinumab, obinutuzumab, cetuximab, erenumab, blinatumomab, romosozumab, mirikizumab, inotuzumab, sacituzumab govitecan, enfortumab vedotin, brentuximab vedotin.

The device 110/210 also includes a needle fluidically connected to the drug reservoir 112/212 and configured to define at least a portion of a fluid flow path between the drug reservoir 112/212 and a subject or patient. The needle and fluid flow path may be variously configured without departing from the scope of the present disclosure, with the needle and flow path being generally configured as described above with regard to the device of FIGS. 1-4 in exemplary embodiments. The housing 116/216 has an adhesive pad 114/214 associated with its lower surface and configured to removably attach to a human body surface. The adhesive can be a pressure sensitive adhesive, particularly any medical grade pressure sensitive adhesive. The adhesive can be rubber, acrylic, and/or silicone based, for example.

The controller 118/218 is configured to control the components of the drug delivery device 110/210 to execute a drug delivery routine. The controller 118/218 may include a microprocessor (which, in fact may include multiple physical and/or virtual processors) and one or more electrical circuits and memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessor to carry out one or more actions as described below.

The device 110/210 may also include at least one indicium associated with a display of the device. The indicium is configured to provide information to a user, which may include for example an indication that the device is ready to begin a drug delivery procedure, that the device is performing a drug delivery procedure, that the device has completed a drug delivery procedure, and/or that there has been an error. The indicium may display or represent the status of the device in any suitable manner. For example, in one embodiment, an indicium may be configured as a shortened message that can display different words, and it may include colors and/or lights to further indicate the state of the device. The indicium may utilize any other type of indication known in the art without departing from the scope of the present disclosure.

The controller 118/218 may be coupled (directly or indirectly connected) to the components of the device 110/210, such as the needle and display. The controller may operate each component, each of which may be an assembly of other devices or equipment, to execute a drug delivery routine. The controller may be programmed to perform other actions as well. Among the components coupled to the controller is a valve 160/260 configured to move to allow the drug to be conveyed from the drug reservoir via an outlet, as will be described in greater detail herein.

The device 110/210 can also include buttons or icons associated with the controller 118/218. The buttons or icons may be variously configured and positioned at any suitable location of the device. The device may include two buttons or icons, for example, with one button/icon being a start button/icon for initializing a procedure and the other button/icon of the set being a stop button/icon for stopping a procedure.

Figure 6:
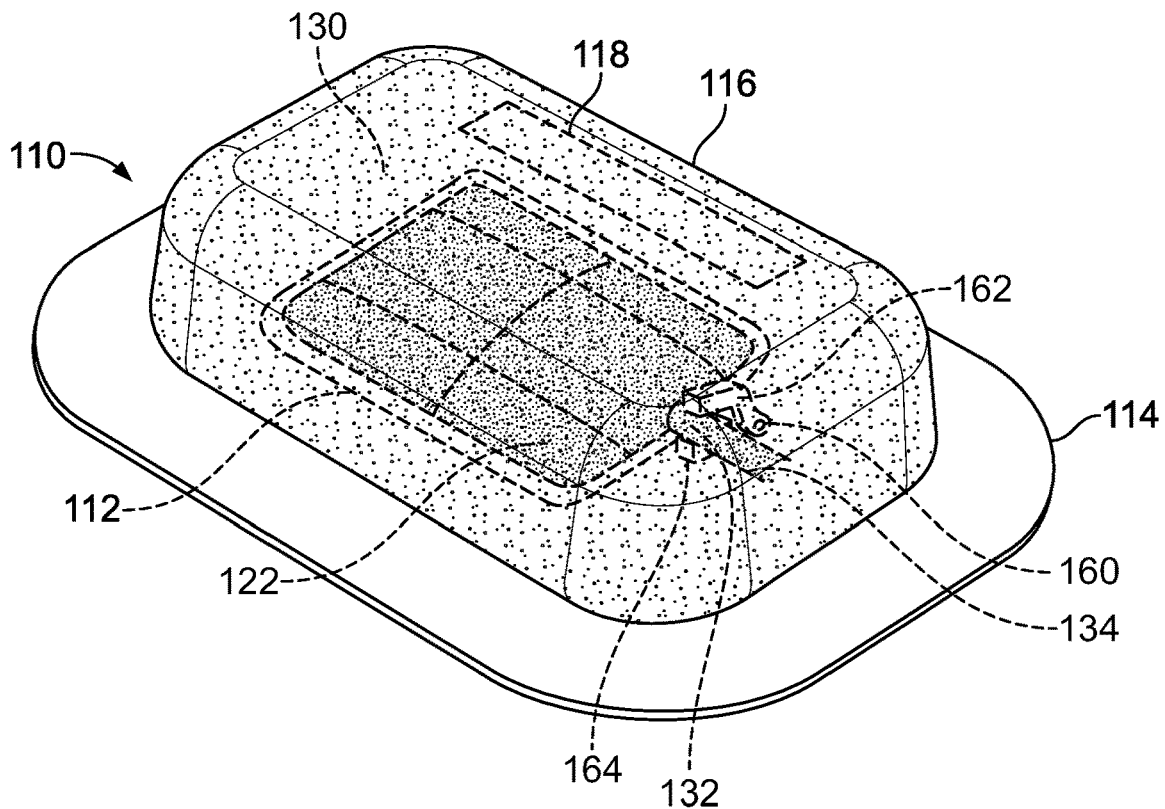
FIG. 6 is a top perspective view of the drug delivery device of FIG. 5, with the valve in an open position.
Figure 7:
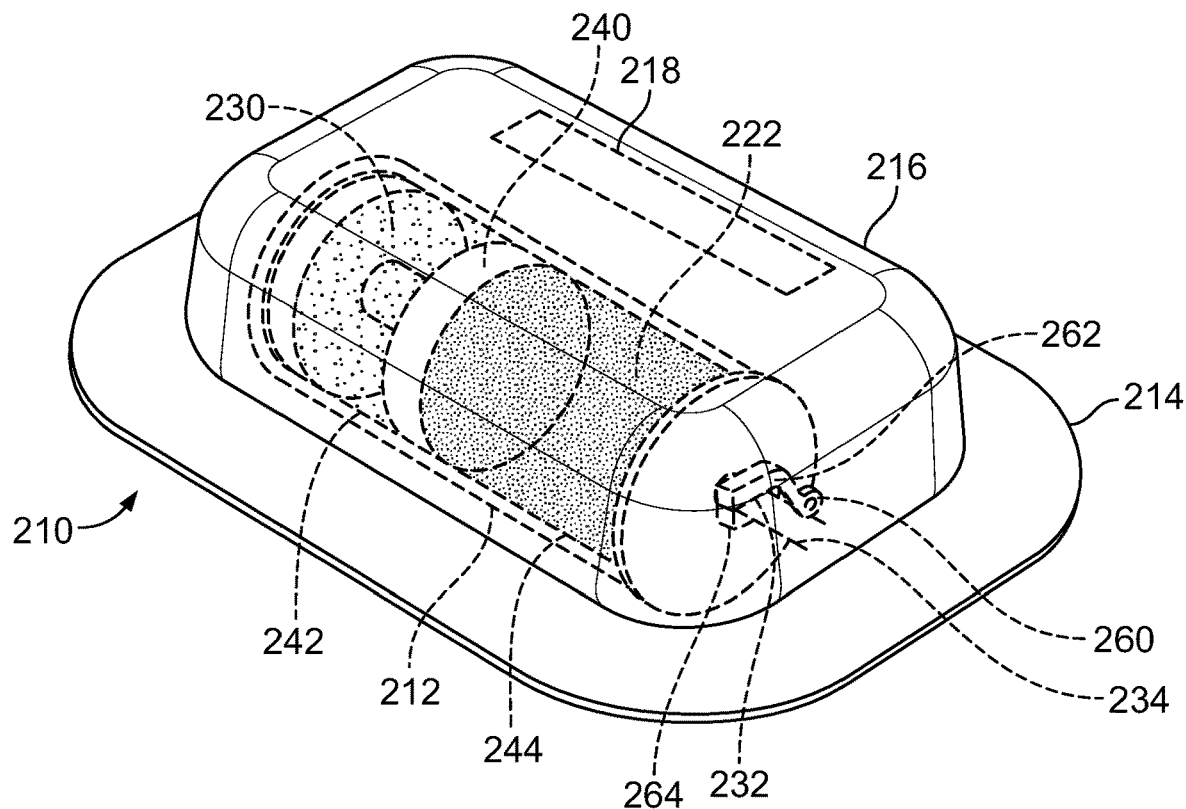
FIG. 7 is a top perspective view of a second exemplary embodiment of a drug delivery device with an improved drug reservoir according to an aspect of the present disclosure, with a valve in a closed position.
Figure 8:
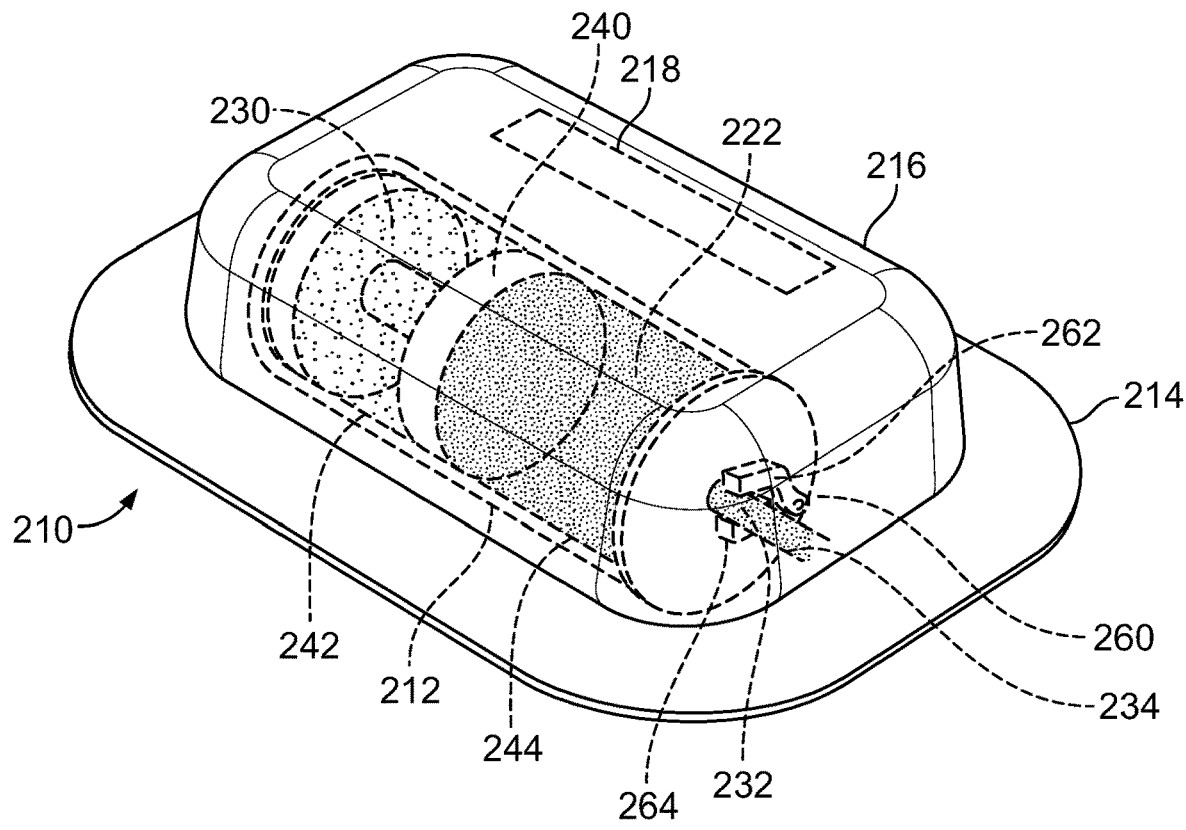
FIG. 8 is a top perspective view of the drug delivery device of FIG. 7, with the valve in an open position.

As noted above, the drug reservoir can be a deformable drug reservoir 112 associated with an external pressurized fluid (FIGS. 5 and 6) or a generally rigid drug reservoir 212 with pressurized fluid within the reservoir (FIGS. 7 and 8). In the embodiment of FIGS. 5 and 6, the drug reservoir 112 is at least partially deformable and/or flexible. The drug reservoir 112 can be any appropriate shape, being generally rectangular with curved or rounded corners in the illustrated embodiment. In an exemplary embodiment, the drug reservoir is configured as a large, flat, flexible bag formed of two films sealed together along at least one edge, and possibly all four edges, of the reservoir or a single film sealed along at least one edge. The reservoir may extend to occupy a significant portion of the length and width of the interior of the housing, which may be advantageous by decreasing the height of the reservoir without decreasing its capacity. For example, the reservoir (when filled with a drug 122) may have a height that is less than half the height of a conventional rigid reservoir (which may be in the range of about 6 mm to about 18 mm). By changing the size/shape of the reservoir from a traditional "syringe-style" reservoir with a round or oval cross-section (as employed in the device of FIGS. 1-4), the delivery device can be much lower profile, making it is less likely to be caught on clothing and/or dislodge, which can lead to leaking.

The drug reservoir 112 may be formed of any suitable material or combination of materials, along with being defined by a single layer or multiple layers of different materials. In an exemplary embodiment, the reservoir is formed of one or more film layers comprised of any one or more of a variety of materials, including thermoplastic materials and elastomers. Suitable materials can include (without limitation) polyethylene, polypropylene, polyurethanes, polyamides, polyesters, ethylene vinyl acetate, natural or synthetic polyisoprene, polybutadiene, polychloroprene, silicone, nitrile rubbers, nylon, olefin, and polyvinyl chloride. The film layer or layers can be comprised of blends or combinations of any of the preceding materials. Different layers of the film can be comprised of the same material or material combinations or different materials or material combinations.

A pressurized fluid 130 (FIG. 6) is positioned within the housing 116, between the housing 116 and the drug reservoir 112 so as to apply a compressive force to at least a portion of the drug reservoir 112. The pressurized fluid 130 can be any applicable fluid known in the art, which may include the pressurized fluid 130 being a gas or liquid. In the case of a pressurized fluid 130 provided as a gas, it may be a compressed gas including, but not limited to, propane, nitrogen, chlorine, helium, and oxygen. In some embodiments, the gas is air or nitrogen. In the case of a pressurized fluid 130 provided as a liquid, it may be a liquified gas, such as anhydrous ammonia, chlorine, propane, nitrous oxide, or carbon dioxide, for example. The pressurized fluid 130 can be pressurized during manufacturing and/or assembly of the drug delivery device 110. This can be accomplished by adding a specific amount of fluid to the device or by adjusting the temperature of the fluid (e.g., by increasing it) to achieve the desired pressure level, for example.

Figure 5:
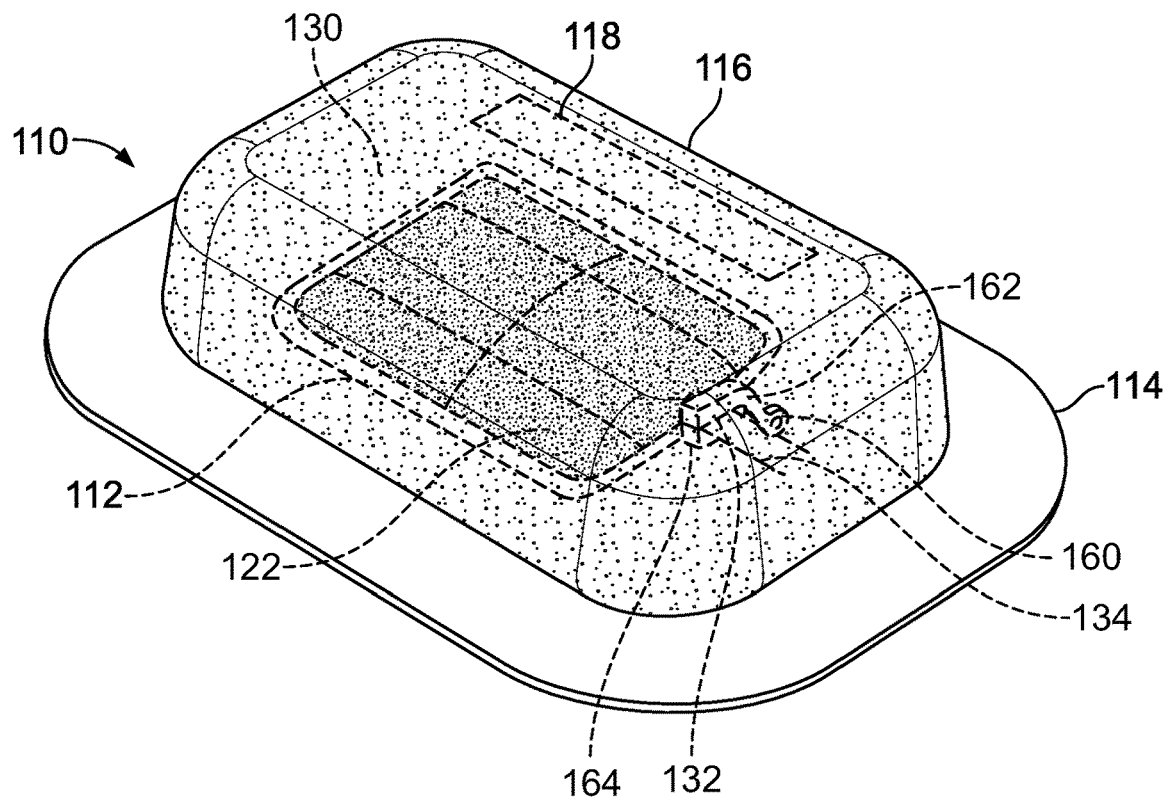
FIG. 5 is a top perspective view of an exemplary embodiment of a drug delivery device with an improved drug reservoir according to an aspect of the present disclosure, with a valve in a closed position.

In the embodiment of FIGS. 7 and 8, the drug reservoir 212 is formed of a generally rigid material, which may include one or more of the materials described above in relation to the deformable drug reservoir 112 of FIGS. 5 and 6, but can also include more rigid materials, such as various plastics, glass, or metal. The drug reservoir 212 is illustrated as a cylinder having a circular or oval cross-sectional shape, but it should be understood that the drug reservoir 212 may be differently shaped without departing from the scope of the present disclosure.

A plunger 240 is movably positioned within the drug reservoir 212 to separate the interior of the drug reservoir 212 into first and second chambers or compartments 242 and 244. A pressurized fluid 230 is maintained within one of the chambers 242 of the reservoir 212, while a liquid drug 222 is positioned within the other chamber 244. The pressurized fluid 230 (which may be configured and provided as described above with regard to the pressurized fluid 130 of the embodiment of FIGS. 5 and 6, for example) tends to urge the plunger 240 in a direction from the first chamber 242 toward the second chamber 242 (i.e., to press the plunger 240 against the liquid drug 222).

Movement of the plunger 240 corresponds to movement or release of the drug 222 from the drug reservoir 212. The plunger 240 is at least movable from a first position to a second position, but may also be movable between the first and second positions (i.e., reversible movement), moving longitudinally relative to the housing of the drug delivery device. The first position of the plunger 240 is farther from an outlet of the drug reservoir 212 than the second position, as can be seen in FIG. 7 (first position) and FIG. 8 (movement from the first position toward the second position), with the second plunger position being between the outlet and the first position, such as directly adjacent to the outlet. The second chamber 244 of the drug reservoir 212 may be at its maximum volume, retaining substantially all of the drug 222, when the plunger 240 is in the first position (with the volume of the first chamber 242 being relatively small), and at its minimum volume, being empty or at least substantially empty, when the plunger 240 is in the second position (with the volume of the first chamber 242 being greater than when the plunger 240 is in its first position). The plunger may also be moved into a third position, between the first and second positions, as shown in FIG. 8. The plunger may further be moved into additional positions without departing from the scope of the present disclosure, with the controller able to stop movement of the plunger in each and/or any of these positions.

The first chamber 242 may either be sealed (entrapping the pressurized fluid 130 within the chamber) or in fluid communication with a source of pressurized fluid 130 (allowing the pressurized fluid to be conveyed between the reservoir and the source to vary the pressure of the fluid within the chamber). When the first chamber 242 is sealed, the force applied by the pressurized fluid 230 to the plunger 240 will remain substantially constant (until the plunger 240 is moved, increasing the volume of the first chamber 242), whereas the force applied to the plunger 240 (at a given plunger position) may be varied when the amount of pressurized fluid 230 in the first chamber 242 may be varied (by alternately conveying an amount of fluid between the first chamber and the fluid source).

In both of the embodiments shown in FIGS. 5-8, the pressurized fluid 130//230 applies force tending to convey a drug 122/222 from the drug reservoir 112/212 via an outlet 132/232. The outlet 132/232 may be located at, incorporated into, or otherwise associated with one edge of the drug reservoir 112/212, for example. In the embodiment of FIGS. 7 and 8, the outlet 232 opens into the second chamber 242 of the drug reservoir 212 (i.e., the chamber in which the drug 222 is positioned). The outlet 132/232 includes an opening of the reservoir 112/212 and may also include a conduit 134/234, such as a tube or tubing that is sized to fit securely in the opening of the drug reservoir 112/212. If provided, the tube or tubing may be formed of any of a variety of materials, including being formed of a generally rigid material or combination of materials and being formed of a generally deformable or flexible material or combination of materials. By way of example, the conduit may be formed of a polymeric material, such as a plastic or rubber polymer, polyvinyl chloride, polyethylene, or a combination of these. The opening of the drug reservoir may also be deformable, particularly when the reservoir itself is formed of a deformable or flexible material. The opening and conduit define a portion of the fluid flow path from the drug reservoir to the needle of the drug delivery device.

Due to the tendency of the pressurized fluid 130/230 to urge the drug 122/222 from the drug reservoir 112/212 via the outlet 132/232, the fluid flow path may include a clamp or valve 160/260 configured to selectively allow and prevent fluid flow through the fluid flow path. The clamp or valve 160/260 may be variously configured and oriented without departing from the scope of the present disclosure, with the clamp or valve 160/260 being associated with the conduit 134/234 of the outlet 132/232 of the drug reservoir 112/212, positioned at or adjacent to the opening of the outlet 132, 232 in the illustrated embodiments. The clamp or valve 160/260 is configured to be moved from a closed condition (FIGS. 5 and 7) to an open condition (FIGS. 6 and 8), with fluid flow through the fluid flow path prevented when the clamp or valve 160/260 is in the closed condition (to retain the drug 122/222 within the reservoir 112/212) and allowed when the clamp or valve 160/260 is in the open condition (to allow the drug 122/222 to be delivered from the reservoir 112/212 to a subject). The clamp or valve 160/260 may be configured to move only from the closed condition to the open condition or to move between the open and closed conditions.

The manner in which the clamp or valve 160/260 regulates fluid flow through the fluid flow path may vary, depending on the configuration of the fluid flow path and the position of the clamp or valve 160/260. For example, in the illustrated embodiments, the clamp or valve 160/260 is associated with the conduit 134/234, which may be configured as a flexible tube. In this case, the clamp or valve 160/260 may be configured as a pinch valve, which may squeeze the conduit 134/234 to close it, thereby preventing fluid flow through the conduit 134/234. The pinch valve 160/260 may have arms 162/262 and 164/264 which are pivotally connected to move from the closed condition (in which they engage and compress the conduit 134/234 to prevent fluid flow therethrough) to the open condition (in which at least one of the arms applies less force to the conduit 134/234 to open to allow fluid to flow through the conduit 134/234). In another embodiment in which the clamp or valve 160/260 is associated with a rigid tube or conduit, the clamp or valve 160/260 may be differently configured to selectively allow and prevent fluid flow through the fluid flow path. This may include the clamp or valve 160/260 being configured as, for example, a glove valve, ball valve, check valve, gate valve, tilting disk check valve, swing-check, or stop-check valve. It is also within the scope of the present disclosure for the clamp or valve 160/260 to be configured as an electromechanical valve, such as a solenoid valve.

In one embodiment, the clamp or valve 160/260 is configured to be moved from the closed condition to the open condition (optionally, between the open and closed conditions) by the controller 118/218. This may be advantageous if the force applied by the pressurized fluid 130/230 does not change during a drug delivery routine, with the controller 118/218 causing the clamp or valve 160/260 to move from the closed condition to the open condition to allow fluid flow out of the drug reservoir 112/212. Alternatively, the clamp or valve 160/260 may be configured to automatically move from the closed condition to the open condition upon an increase in pressure or force applied to the clamp or valve 160/260 by the drug 122/222. This may be advantageous if the force applied by the pressurized fluid 130/230 may increase during a drug delivery routine, in which case the clamp or valve 160/260 may be configured as a check valve, being closed when the applied force is lower than a threshold amount and open when the applied force is greater than the threshold amount.

In any case, it will be seen that the pressurized fluid, drug reservoir, valve, and controller work in conjunction to convey the drug from the drug reservoir via the outlet and to the needle and patient during a drug delivery routine. The controller opens and closes the valve selectively (either directly or by causing a change in the force applied by the pressurized fluid) to selectively allow and prevent the drug from flowing out of the drug reservoir. Movement of the clamp or valve between open and closed conditions can be varied based on the selected drug delivery routine. For example, the clamp or valve can be moved to the open position and remain open during the duration of the drug delivery routine. The clamp or valve can also be moved back and forth between the open and closed positions during the drug delivery routine, with the change in position being based on any of a number of considerations. For example, the controller may move the clamp or valve from the open condition to the closed condition when a predetermined amount of the drug is conveyed from the drug reservoir or after a predetermined amount of time after moving the clamp or valve from the closed condition to the open condition. The change between the closed and open conditions can take place multiple times during a drug delivery routine, with the movement of the clamp or valve taking place in an irregular pattern or regular pattern, such as a duty cycle, depending on the needs of the routine.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A drug delivery device comprising:
   a housing;
   an adhesive pad associated with a lower surface of the housing and configured to removably attach to a human body surface;
   a deformable drug reservoir positioned within the housing and including an outlet with a valve;
   a needle fluidically connected to the outlet of the drug reservoir and configured to define at least a portion of a fluid flow path between the drug reservoir and said human body surface;
   a controller configured to execute a drug delivery routine; and
   a pressurized fluid positioned between the housing and the drug reservoir in a space defined in part by the drug reservoir, with the pressurized fluid exerting a compressive force on the drug reservoir, wherein the controller is configured to control the valve to move from a closed condition to an open condition during said drug delivery routine so as to allow the pressurized fluid to deform the drug reservoir, thereby conveying a drug out of the drug reservoir via the outlet.

2. The drug delivery device of claim 1, configured to deliver a drug comprising pegfilgrastim.

3. The drug delivery device of claim 1, wherein the controller is configured to control the valve to move from the closed condition to the open condition a single time and remain open during the drug delivery routine.

4. The drug delivery device of claim 1, wherein the controller is further configured to control the valve to move from the open condition to the closed condition to prevent further removal of the drug from the drug reservoir.

5. The drug delivery device of claim 4, wherein the controller is configured to move the valve from the open condition to the closed condition when a predetermined amount of the drug is conveyed from the drug reservoir.

6. The drug delivery device of claim 4, wherein the controller is configured to move the valve from the open condition to the closed condition a predetermined amount of time after moving the valve from the closed condition to the open condition.

7. The drug delivery device of claim 1, wherein the controller is configured to control the valve to move between the closed condition and the open condition a plurality of times during the drug delivery routine.

8. The drug delivery device of claim 7, wherein the controller is configured to control the valve to move between the closed condition and the open condition in a regular pattern.

9. The drug delivery device of claim 8, wherein the pattern is a duty cycle.

10. The drug delivery device of claim 1, wherein
    at least a portion of the outlet is deformable, and
    the valve comprises a pinch valve configured to engage and deform the outlet in the closed condition.

11. A drug delivery device comprising:
    a housing;
    an adhesive pad associated with a lower surface of the housing and configured to removably attach to a human body surface;
    a drug reservoir positioned within the housing and including an outlet with a valve;
    a plunger positioned within the drug reservoir, separating an interior of the drug reservoir into first and second chambers;
    a needle fluidically connected to the outlet of the drug reservoir and configured to define at least a portion of a fluid flow path between the drug reservoir and said human body surface;
    a controller configured to execute a drug delivery routine; and
    a pressurized fluid sealed within the first chamber of the drug reservoir and exerting a force on the plunger, wherein
       the amount of pressurized fluid in the first chamber is constant throughout the drug delivery routine, and
       the controller is configured to control the valve to move from a closed condition to an open condition during said drug delivery routine so as to allow the pressurized fluid to move the plunger toward the outlet, thereby conveying a drug positioned within the second chamber out of the drug reservoir via the outlet.

12. The drug delivery device of claim 11, configured to deliver a drug comprising pegfilgrastim.

13. The drug delivery device of claim 11, wherein the controller is configured to control the valve to move from the closed condition to the open condition a single time and remain open during the drug delivery routine.

14. The drug delivery device of claim 11, wherein the controller is further configured to control the valve to move from the open condition to the closed condition to prevent further removal of the drug from the drug reservoir.

15. The drug delivery device of claim 14, wherein the controller is configured to move the valve from the open condition to the closed condition when a predetermined amount of the drug is conveyed from the drug reservoir.

16. The drug delivery device of claim 14, wherein the controller is configured to move the valve from the open condition to the closed condition a predetermined amount of time after moving the valve from the closed condition to the open condition.

17. The drug delivery device of claim 11, wherein the controller is configured to control the valve to move between the closed condition and the open condition a plurality of times during the drug delivery routine.

18. The drug delivery device of claim 17, wherein the controller is configured to control the valve to move between the closed condition and the open condition in a regular pattern.

19. The drug delivery device of claim 18, wherein the pattern is a duty cycle.

20. The drug delivery device of claim 11, wherein
at least a portion of the outlet is deformable, and
the valve comprises a pinch valve configured to engage and deform the outlet in the closed condition.

* * * * *